United States Patent [19]

Wakayama et al.

[11] Patent Number: 4,771,121
[45] Date of Patent: Sep. 13, 1988

[54] SUBSTANCE GIF-2 AND PROCESS FOR PRODUCTION OF THE SAME

[75] Inventors: Sachio Wakayama, Tokyo; Fumiyasu Ishikawa, Kanagawa; Kunio Oishi, Tokyo, all of Japan

[73] Assignee: Kibun Co., Ltd., Tokyo, Japan

[21] Appl. No.: 807,066

[22] PCT Filed: Mar. 29, 1985

[86] PCT No.: PCT/JP85/00154
§ 371 Date: Nov. 27, 1985
§ 102(e) Date: Nov. 27, 1985

[87] PCT Pub. No.: WO85/04883
PCT Pub. Date: Nov. 7, 1985

[30] Foreign Application Priority Data

Apr. 25, 1984 [JP] Japan .................................. 59-82000

[51] Int. Cl.$^4$ ................................. C07K 5/12
[52] U.S. Cl. ..................................... 530/317
[58] Field of Search ......................... 530/317

[56] References Cited

PUBLICATIONS

Chem. Abstr. vol. 104 (1986), 67506.

Primary Examiner—Delbert R. Phillips
Attorney, Agent, or Firm—Wenderoth, Lind & Ponack

[57] ABSTRACT

A substance GIF-2 having bacteriostatic activities and a process for producing the same are disclosed.

GIF-2 is produced by culturing bacteria capable of producing GIF-2 and belonging to genus Bacillus, and isolating GIF-2 from the culture medium. GIF-2 is presumed to have the following structure:

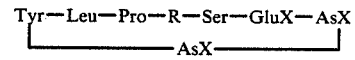

wherein one of three X's is an amido bond and R is a β-amino acid residue represented by the formula 1 Claim, 2 Drawing Sheets

SUBSTANCE GIF-2 AND PROCESS FOR PRODUCTION OF THE SAME

THE FIELD OF THE INVENTION

This invention relates to a substance GIF-2 having an antimicrobial activity and to a process for production of the substance.

DESCRIPTION OF THE INVENTION

The inventors of this invention have been undertaking studies on microorganisms which are parasitic to insects and have occasionally found certain bacteria having an antimicrobial activities to organisms. After screening such bacteria, they identified them as bacteria belonging to the species *Bacillus cereus*. They have continued their studies on the antimicrobial substances produced by the bacteria and isolated a novel substance which they have named GIF-2.

The bacteria which are useful in this invention involve any species of bacteria capable of producing GIF-2. One example of such bacteris is *Bacillus cereus* SW which was first screened by the inventors and deposited with the Fermentation Research Institute, Japan as International Deposition Acceptance No. FERM BP-746 under the Budapest Treaty. The microbiological characteristics of *Bacillus cereus* SW are as follows:

| | |
|---|---|
| Gram stain | + |
| Spore stain | + |
| V-P reaction | + |
| Catalase test | + |
| Oxidase test | + |
| Growth at 50° C. | − |
| Heat resistance test (10° C., 30 min.) | + (growing) |
| Egg-Yolk reaction | + |

Bacteria such as *Bacillus cereus* SW are cultured in a suitable media. Some examples of the media are as follows:

| | |
|---|---|
| Medium 1 | |
| polypepton | 3% |
| yeast extract | 0.5% |
| NaCl | 0.5% |
| deionized water | 96% |
| | (pH = 7.0) |
| L-medium | |
| bacto-trypton | 1% |
| yeast extract | 0.5% |
| NaCl | 0.5% |
| | (pH = 7.0) |
| MY-medium | |
| lactose | 1% |
| polypepton | 0.5% |
| yeast extract | 0.3% |
| malt extract | 0.3% |
| (The pH is adjusted to 7.0 with 0.05 M phosphoric acid buffer.) | |

In addition to these culture media exemplified above, suitable media such as media for bacteria which contain appropriate amounts of carbon source, nitrogen source, and micronutrients may be used in this invention.

The bacteria may be cultured at 20° to 40° C., preferably at 25° to 30° C. for 2 to 3 days under aerobic conditions such as by shaking culture, aeration culture, stationary culture and the like.

After culturing, the culture medium is centrifuged, for example, at 7,500 rpm for 10 min., to remove bacterial cells. The medium is preferably concentrated if necessary and, after adding calcium chloride to the medium in such an amount as to give 1%, the resulting precipitate is recovered by centrifugation, for example at 2,500 rpm for 10 min. The collected precipitate is dissolved in 100 mM EDTA-0.05M tris-HCl buffer (pH 8.0) and the solution is dialyzed against 0.05M phosphoric acid buffer (pH 7.0). After dialysis, ethanol is added to the dialyzate to give 80%, and the resulting precipitate is then removed. The supernatant is evaporated under reduced pressure to dryness and the residue is dissolved in a deionized water. The pH is adjusted to 3 by addition of hydrochloric acid to form a precipitate. The precipitate is recovered and dissolved in a 0.05M $NaHCO_3$ aqueous solution, and the solution is dialyzed against deionized water, the dialyzate then being charged into and passed through a column with Sephadex G-100/$H_2O$.

Ethanol is added to the eluate solution to give 80% and the mixture in allowed to stand at 4° C. for 2–3 days to give a white crystalline precipitate.

After drying the precipitate under reduced pressure, the product GIF-2 is given as white prismatic microcrystals by microscopic observation.

GIF-2 has the following physiochemical properties.

1. Molecular weight: 1057 by Mass spectrometer
2. Color and appearance: White prismatic microcrystals
3. Melting point: 210°–215° C. (light brown, slightly shrinked), 234°–239° C. (dark brown), 240°–245° C. (carbonized)
4. UV absorption spectrum: Shown in FIG. 1 measured as a 2.8% aqueous solution.
5. IR spectrum: Shown in FIG. 2
6. Solubilities in solvents: Soluble in water, methanol, ethanol, and t-butanol; insoluble in n-butanol, acetone, ethyl acetate, ether, chloroform, benzene, carbon tetrachloride, and petroleum ether
7. Color change test:

| | |
|---|---|
| CBB test | + |
| Xanthoprotein test | + |
| Adamkiewitz test | − |
| Earlich test | − |
| Biuret test | + |

8. Other property: A solution of this substance in water (1.4 mg/ml) has a pH of 7.6
9. Amino acid composition: The amino acid composition by an amino acid analyzer is as follows:

| Amino acid | Moler ratio |
|---|---|
| AsX | 2 |
| Ser | 1 |
| GluX | 1 |
| Leu | 1 |
| Tyr | 1 |
| Pro | 1 | wherein one of three X's has an amido bond, and in addition to the above amino acids, one molecule of β-amino acid is found by a mass spectrometer.

10. Presumed Structure:

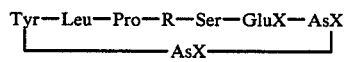

wherein one of three X's is an amido bond and R is a β-amino acid residue represented by the formula

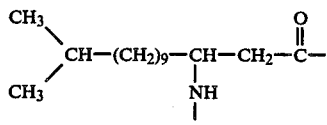

Figure 1:
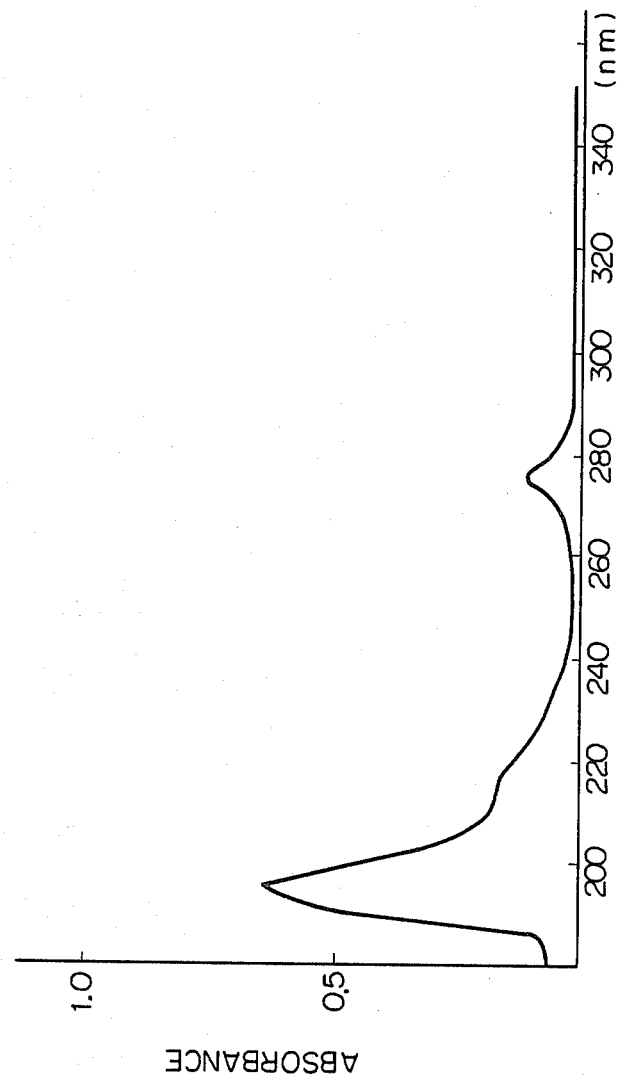
FIG. 1 is a chart showing U.V. absorption spectrum of GIF-2.

The antimicrobial activities of GIF-2 are confirmed and shown hereunder.

The antimicrobial activities in relation to various microorganisms were tested by the use of the following culture media and the results are shown in Tables 1 to 4 below.

| Culture medium for bacteria in general | |
|---|---|
| Meat extract | 10 g |
| Peptone | 10 g |
| NaCl | 5 g |
| Water | 1 l |
| | (pH = 7.2) |
| Culture medium for mycobacteria | |
| Glycerol | 10 g |
| Polypepton | 10 g |
| Casamino acid | 5 g |
| Yeast extract | 5 g |
| Na$_2$HPO$_4$ | 0.5 g |
| Water | 1 l |
| | (pH = 7.2) |
| Culture medium for fungi | |
| Lactose | 10 g |
| Polypepton | 5 g |
| Yeast extract | 3 g |
| Malt extract | 3 g |
| 0.05 M phosphoric acid buffer | 1 l |
| | (pH = 7.0) |

The following microorganisms were cultured on a microtiter plate at 27° C. for 3 to 7 days. The minimum inhibitory concentration (MIC) of GIF-2 with respect to the microorganisms is shown in Tables 1 to 4 below.

TABLE 1

| Strain | | M.I.C. (μg/ml) |
|---|---|---|
| Bacillus subtilis | IAM 1206 | >625 |
| | IAM 1069 | >625 |
| | IAM 1145 | >625 |
| | IAM 1168 | >625 |
| | IAM 1169 | >625 |
| | IAM 1207 | >625 |
| | IAM 1212 | >625 |
| | IAM 1213 | >625 |
| | IAM 1259 | >625 |
| | IAM 1260 | >625 |
| | IAM 11060 | >625 |
| | IAM 12021 | >625 |
| | IAM 12118 | >625 |
| Bacillus licheniformis | IAM 11054 | >625 |
| Bacillus polymixa | IAM 1210 | >625 |
| Bacillus amyloliquefaciens | IAM 1521 | >625 |
| Bacillus cereus | IAM 1029 | >625 |
| | IAM 1072 | >625 |
| | IAM 1110 | >625 |
| | IAM 1656 | >625 |
| | IAM 1729 | >625 |
| Bacillus coagulans | IAM 1194 | >625 |
| Bacillus megaterium | IAM 1166 | 19 |
| Bacillus cereus SW | | >625 |

TABLE 2

| Strain | | M.I.C. (μg/ml) |
|---|---|---|
| Escherichia coli | IAM 1268 | >625 |
| Enterobacter aerogenes | IAM 12348 | >625 |
| Klebsiella pneumoniae | IAM 1063 | >625 |
| Serratia marcescens | IAM 12142 | >625 |
| Proteus vulgaris | IAM 1025 | >625 |
| Pseudomonas aeruginosa | PAO 1 | >625 |
| Staphylococcus aureus | NIHJ 209P | >625 |
| Micrococcus luteus | IAM 1056 | >625 |
| Arthrobacter nicotianae | IAM 12342 | >625 |
| Nocardia opaca | IAM 12123 | >625 |
| Mycobacterium phlei | AU 3368 | >625 |
| " | AU 1574 | >625 |

TABLE 3

| Strain | | M.I.C.(μg/ml) |
|---|---|---|
| Conidiobolus lamprauges | sp. No. 454 | 19.5 |
| | ATCC 28996 | 39 |
| | ATCC 28997 | 19.5 |
| | CBS 153 | 19.5 |
| Conidiobolus thromboides | ATCC 12587 | 39 |
| Conidiobolus nanodes | CBS 154 | 19.5 |
| Conidiobolus nanodes | CBS 183 | 19.5 |
| Conidiobolus chlamydosporus | CBS 167 | 39 |
| Fusarium oxysporum | IAM 5009 | 39 |

TABLE 4

| Strain | | M.I.C. (μg/ml) |
|---|---|---|
| Aspergillus fumigatus | IAM 2004 | 78 |
| Aspergillus nidulans | IAM 2006 | 39 |
| Aspergillus oryzae | IAM 2640 | 156 |
| Chaetomium globosum | IAM 8059 | 78 |
| Eurotium chevalieri | IFO 4928 | 19.5 |
| | ATCC 16496 | 39 |
| Gliocladium virens | IAM 5061 | 39 |
| Mucor rouxianus | IAM 6131 | 78 |
| Mucor javanicus | IAM 6087 | 156 |
| Myrothecium verrucaria | IAM 5063 | 78 |
| Penicillium chrysogenum | IAM 7106 | 39 |
| Cryptococcus luteolus | IAM 12207 | 19.5 |
| Debaryomyces castellii | IAM 4977 | 78 |
| Hansenula anomala | IAM 4967 | 39 |
| Hansenula wingei | IAM 4983 | 19.5 |
| Kloeckera africana | IAM 4984 | 39 |
| Saccharomyces cerevisiae | IAM 4125 | 39 |
| Torulopsis colliculosa | IAM 4188 | 39 |

This invention is further illustrated by the following Example.

EXAMPLE

The strain *Bacullus cereus* SW, FERM BP-746 was inoculated on Medium 1 described above and cultured at 27° C. for 3 days by shaking culture.

The resulting culture medium was centrifuged at 7,500 rpm for 10 min., and to the supernatant was added calcium chloride to give 1%. The resulting precipitate was recovered by centifugation at 2,500 rpm for 10 min. The precipitate was dissolved in a 100 mM EDTA- 0.05M tris-Hcl buffer (pH 8.0) and the solution was dialyzed against a 0.05M phosphoric acid buffer, and ethanol was added to the dialyzed solution to give a final concentration of 80%.

The resulting precipitate was removed, the supernatant was evaporated under reduced pressure to dryness and the residue was dissolved in deionized water. The pH of the solution was then adjusted to 3 by addition of hydrochloric acid. The resulting precipitate was dissolved in a 0.05M NaHCO$_3$ aqueous solution and the solution was dialyzed against deionized water. The dialyzate solution was then charged into and passed through a column with Sephadex G-100/H$_2$O. Ethanol was added to the eluate to give a concentration of 80%, and the mixture was allowed to stand at 4° C. for 2 to 3 days to form a white crystalline precipitate.

The precipitate was evaporated under reduced pressure, to dryness and the presence of GIF-2 was confirmed as white prismatic microcrystals by microscopic observation.

Figure 2:
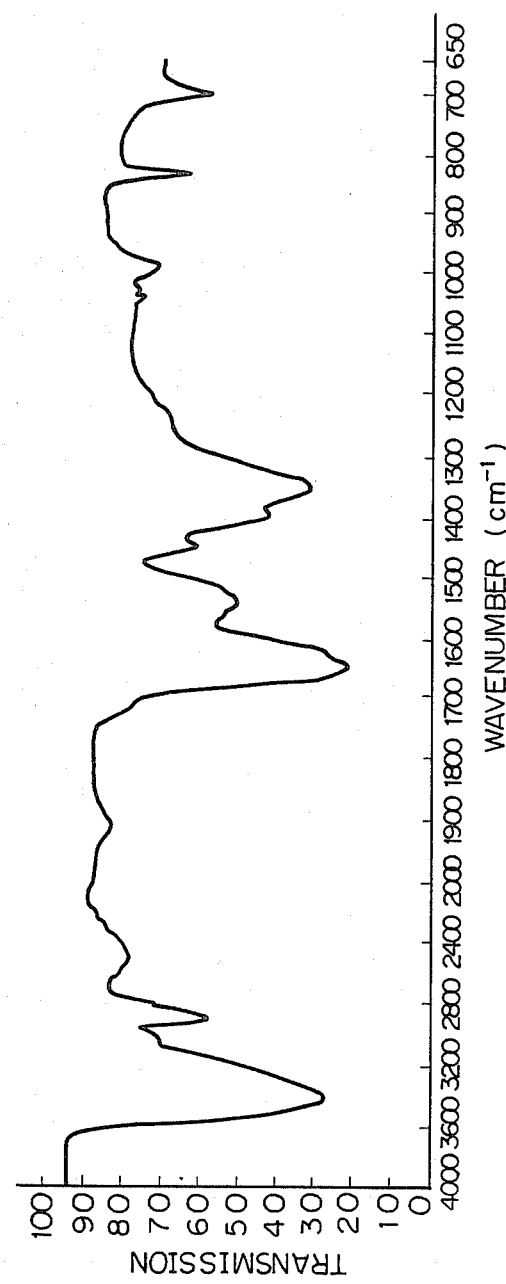
FIG. 2 is a chart showing I.R. absorption spectrum of GIF-2.

We claim:

1. A substance GIF-2 having the following physio-chemical properties:
   (1) Molecular weight: 1057 by Mass spectrometer
   (2) Color and appearance: White prismatic microcrystals
   (3) Melting point: 210°–215° C. (light brown, slightly shrinked), 234°–239° C. (dark brown), 240°–245° C. (carbonized)
   (4) UV absorption spectrum: shown in FIG. 1 measured as a 2.8% aqueous solution
   (5) IR spectrum: shown in FIG. 2
   (6) Solubilities in solvents: soluble in water, methanol, ethanol, and t-butanol; insoluble in n-butanol, acetone, ethyl acetate, ether, chloroform, benzene, carbon tetrachloride, and petroleum ether
   (7) Color change test:

| | |
|---|---|
| CBB test | + |
| Xanthoproteic test | + |
| Adamkiewitz test | − |
| Earlich's test | − |
| Buret test | + |

(8) Other property: A solution of this substance in water (1.4 mg/ml) has a pH of 7.6
   (9) Amino acid composition: The amino acid composition by an amino acid analyzer is as follows:

| Amino acid | Moler ratio |
|---|---|
| AsX | 2 |
| Ser | 1 |
| GluX | 1 |
| Leu | 1 |
| Tyr | 1 |
| Pro | 1 | wherein one of three X's has an amido bond, and in addition to the above amino acids, one molecule of β-amino acid is found by a mass spectrometer.
   (10) Presumed Structure:

$$\text{Tyr—Leu—Pro—R—Ser—GluX—AsX} \atop {\underline{\hspace{1cm}\text{AsX}\hspace{1cm}}}$$

wherein one of three X's is an amido bond and R is a β-amino acid residue represented by the formula $$\begin{array}{c}CH_3 \\ \phantom{x}\diagdown \\ \phantom{xx}CH-(CH_2)_9-CH-CH_2-\overset{O}{\overset{\|}{C}}- \\ \phantom{x}\diagup \phantom{xxxxxxxxxx} | \\ CH_3 \phantom{xxxxxxxxxx} NH \\ \phantom{xxxxxxxxxxxxx} |\end{array}$$

* * * * *